US00PP16309P3

(12) United States Plant Patent
Orton et al.

(10) Patent No.: US PP16,309 P3
(45) Date of Patent: Mar. 7, 2006

(54) **INTERSPECIFIC *CORNUS* HYBRID DESIGNATED KN30-8**

(50) Latin Name: *(Cornus kousa×C. nuttallii)×C. Kousa*
Varietal Denomination: KN30-8

(75) Inventors: Elwin R. Orton, Hillsborough, NJ (US); David A. Gant, Wall Township, Monmouth County, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 114 days.

(21) Appl. No.: 10/741,623

(22) Filed: Dec. 19, 2003

(65) Prior Publication Data

US 2005/0138707 P1 Jun. 23, 2005

(51) Int. Cl.
*A01H 5/00* (2006.01)

(52) U.S. Cl. ..... Plt./220
(58) Field of Classification Search ..... Plt./220
See application file for complete search history.

(56) References Cited

U.S. PATENT DOCUMENTS

PP2,413 P * 6/1964 Fill ..... Plt./220
PP7,205 P * 3/1990 Orton, Jr. ..... Plt./220
PP7,206 P * 3/1990 Orton, Jr. ..... Plt./220
PP7,207 P * 3/1990 Orton, Jr. ..... Plt./220
PP7,210 P * 4/1990 Orton, Jr. ..... Plt./220
PP14,537 P2 * 2/2004 Elsley ..... Plt./220

OTHER PUBLICATIONS http://www.landsteward.com/page.cfm/10331?template=Plant.*

TESS United States Trademark Application Serial No. 76556303 'Venus'.*

UPOV ROM GTITM Computer Database, GTI Jouve Retrieval Software 2004/04 Citations for 'Constellation', 'Stellar Pink', 'Stardust', 'Eddie's White Wonder', and 'Aurora'.*

* cited by examiner

*Primary Examiner*—Kent Bell
*Assistant Examiner*—W. C. Haas
(74) *Attorney, Agent, or Firm*—James A. Lucas; Driggs, Lucas, Brubaker & Hogg Co., L.P.A.

(57) ABSTRACT

An advanced generation interspecific hybrid of (*Cornus kousa×C. nuttallii*) that is distinguished by its exceptionally high vigor, superior foliage, floriferous display of very attractive and exceptionaly large white floral bracts, high level of winter hardiness, good drought tolerance and high resistance to the incitants of powdery mildew and dogwood anthracnose.

2 Drawing Sheets

Botanical designation: (*Cornus kousa×C. nuttallii*)×*C. kousa.*
Variety denomination: KN30-8

BACKGROUND OF THE INVENTION

This new cultivar is the product of a long standing detailed program of interspecific hybridization and selection of dogwoods, in this instance a cross of an $F_1$ interspecific hybrid of a *Cornus kousa×C. nuttallii* backcrossed to an unrelated *Cornus kousa*. The progeny were carefully retained and characteristics analyzed for their differences and outstanding value as potential commercial varieties or cultivars.

We have selected the particular seedling hereof from certain progeny grown in a cultivated area and, as a result, have in turn caused the same to be asexually reproduced by grafting (usually T-budding or chip-budding). It also can be propagated by softwood cuttings. The reproduction and actual growth and selection of the new cultivar took place in the vicinity of New Brunswick, N.J. and has been found to be distinctive as to its winter-hardiness in that area, USDA Plant Hardiness Map Zone 6a.

As will be understood from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore suggested.

SUMMARY OF THE INVENTION

The variety was originated or discovered on Horticulture Farm No. 1 of Rutgers University, New Brunswick, N.J. 08901, Middlesex County. This seedling resulted from a controlled cross made Jun. 2, 1983, between an unpatented hybrid *Cornus kousa×C. nuttallii* plant (seed parent) and a *C. kousa* plant (pollen parent). The complete parentage of the claimed plant can be summaed as follows:

(*Cornus kousa* 'Chinensis'×*C. nuttallii* 'Goldspot')×*C.kousa* 'Rosea'.

The antecedent cultivars 'Chinensis', 'Goldspot' and 'Rosea' are all unpatented.

The seedling which became this new variety germinated during April 1984, was transplanted ftom the seedling flat to a one-gallon container in May 1984 and subsequently grown in progressively larger containers until April 1986, when it was transplanted to field No. 20 at the animal research farm of the NJ Agricultural Experiment Station in North Brunswick, N.J. and is growing there now as a 20-year-old tree. It has also been propagated by nurserymen in Tennessee, Oregon, and California under formal testing agreement with the NJAES, Cook College/Rutgers University. To the best of our knowledge, this new variety is the first reported advanced generation interspecific hybrid of these two species.

BRIEF DESCRIPTION OF THE DRAWINGS

This new cultivar of dogwood is illustrated by the accompanying photographic drawings, depicting the plant by the best possible color representation using color photography. All color references below are measured against The Royal Horticultural Society (R.H.S.) Colour Chart. Colors are approximate as color depends on horticultural practices, such as light level and fertilization rate, among others.

BOTANICAL DESCRIPTION OF THE INVENTION

PLANT

Figure 1:
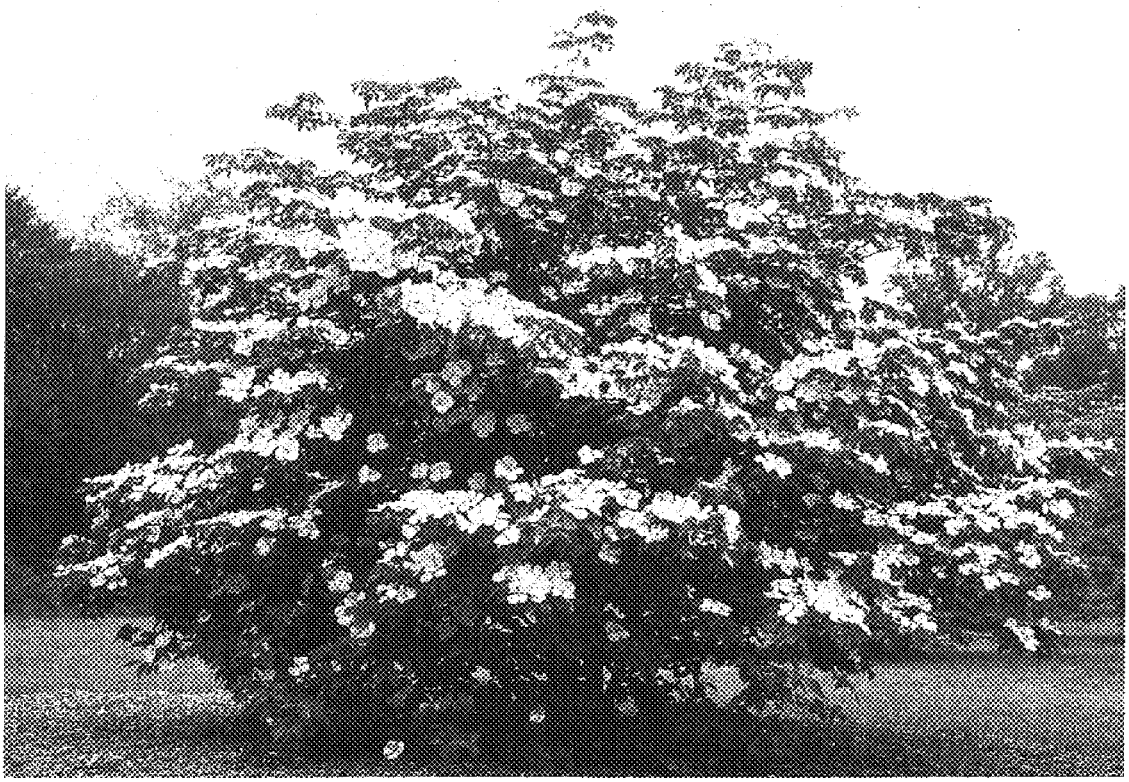
FIG. 1 shows a dogwood tree of the present invention after 20 growing seasons.
Figure 2:
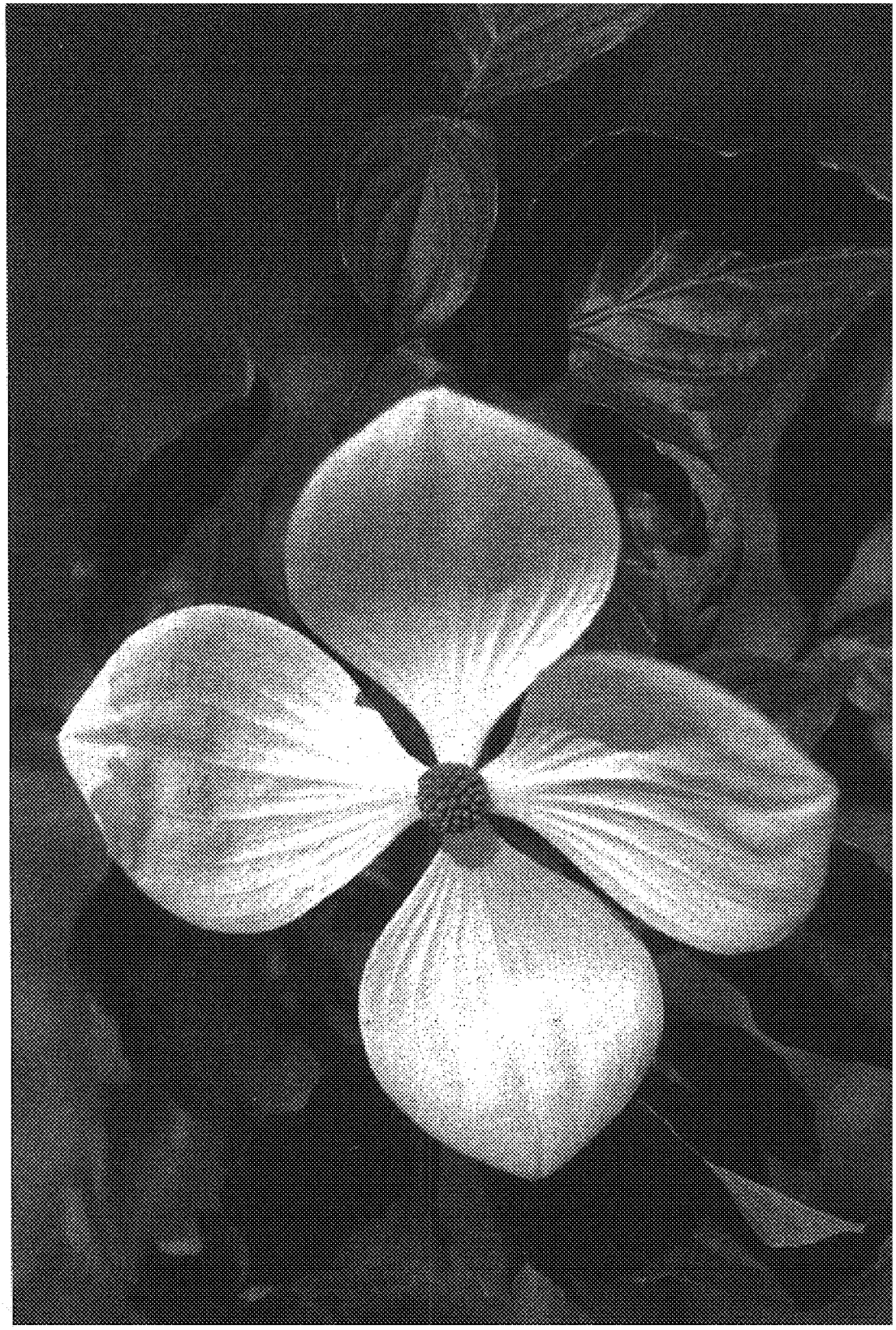
FIG. 2 shows a single flower head of the tree shown in FIG. 1 taken at the time of floral display, and indicates the color and shape of the floral bracts.

Form: Tree.

Growth habit: Dense tree branched low to ground with upright branches which form a rounded head wider than tall. Very vigorous.

*Height.*—5.48 meters at 20 years.

*Spread.*—6.55 meters at 20 years.

Plant vigor: Plants of this new hybrid variety are much more vigorous than plants of current varieties known to the inventors of *C. kousa*. One year budded liners (either *C. kousa* or *C. florida* rootstock) produced in either Boring, Oreg. or Winchester, Tenn. have averaged 1.2 meters tall and are stout and branched.

Cold hardiness: Original seedling has suffered no winter injury during the 18 years it has been observed in the field at North Brunswick, N.J. in USDA Plant Hardiness Map Zone 6a (−5° to −10° F.).

Resistance to insects and disease: No insect or disease problems were observed during the 18 years the original seedling of the variety 'KN30-8' has been tested in the field.

Trunk: Circumference of the crown of the original seedling at the soil level was 1.35 m after 20 growing seasons.

*Color.*—Between 197C and 197D Greyed-Green Group.

*Texture.*—Sandpaper rough, bark exfoliating at basal 0.46 m of trunk area.

Branches:

*Color.*—Closest to 200B, Brown Group.

*Texture.*—Smooth, with small rough bumps (lenticels).

*Crotch angle.*—45°.

*Lenticels.*—Abundant. The average (n=4) of lenticels per $cm^2$ is 103.75 based on a range of 4 sample areas between 74 $cm^2$–164 $cm^2$.

*Internode length.*—6.5–15 cm.

FOLIAGE

Leaf arrangement: Opposite.

Leaf size — blade:

| Year | n | average length (cm) | average width (cm) |
|---|---|---|---|
| 1998 | 25 | 13.24 | 7.68 |
| 2001 | 26 | 10.59 | 5.99 |
| 2002 | 10 | 15.30 | 9.09 |

Wherein n are the number of observations

*Shape.*—Oval to obovate.

*Tip.*—Apiculate.

*Base.*—Attenuate-acuminate.

*Margin.*—Mildly wavy.

Texture: Leaves heavily textured with prominent midrib on abaxial surface; average of 5, sometimes 6, secondary vein pairs. Both surfaces downy, more so beneath, due to many fine, short, whitish hairs.

Other features: Dense tufts of long, brown hairs at axils of the uppermost 3–4 vein pairs.

Quantity: Many, densely foliaged.

Coloration: Solid.

Mature foliage color — adaxial: 139A Green Group. Abaxial: 137C Green Group.

Autumn foliage color at New Brunswick, N.J.:

*Adaxial surface.*—September 10 through October — 137A Green Group; November — Foliage quite attractive but leaves at base of tree and interior of plant green (137A Green Group). Other leaves still predominantly green but mottled with other colors: mostly 187A and 185A Greyed Purple Group with a mottle of 13A Yellow, 17C Yellow-Orange, 42A Red, and 46A Red.

*Abaxial surface.*—138C Green Group.

Leaf color is clearly dependent on many environmental factors such as soil type, exposure to sun, air temperature, day length, available water and nutrients. Thus, leaf color may vary from one area to another. Veins and ribs: The basal 3–4 cm of the midrib of the leaves sometimes shows a little yellow streak closest to Yellow-Group 8D.

Petiole: Color at New Bunswick, N.J.

*May.*—144B Yellow-Green Group.

*June.*—143C Yellow-Green Group.

*September.*—145A Yellow-Green Group.

*October.*—144A Yellow-Green Group with a little 47B Red Group and 53A Red Group.

Disease resistance: Asexually propagated plants of our new hybrid variety have been tested in New Brunswick, N.J. (18 years) and in Boring, Oreg. and Winchester, Tenn. (10 years) with no evidence of susceptibility to Powdery Mildew or Dogwood Anthracnose.

INFLORESCENCE

Location where observations were made: Animal Research Farm, NJAES, North Brunswick, N.J.

Type of inflorescence: Flower head. Dense, rounded mound.

Over-wintering flower buds: 5.6 mm high and 6.3 mm wide (n=10 measurements taken).

Peduncle: In winter months, 1–2 cm long and 3.1 cm wide. Is completely covered, or enclosed, by typically 2, sometimes 3, pairs of opposing, appressed bracts approximately 9.1 mm long and 7.6 mm wide. These vegetative bracts are closely telescoped on the peduncle, are uniformly wide at the basal 60 percent, close in slightly and taper to a blunt apex. Their color is 185A Greyed-Purple at base and center and 177B Grey-Orange at the tips and along the margins.

Size at time of flowering — (late May — early June):

| Year | n | Length (cm) average | Width (mm) average |
|---|---|---|---|
| 2002 | 20 | 5.50 | 2.85 |
| 2003 | 35 | 7.64 | 2.89 |

Peduncle length in 'KN30-8' is not significantly different from that in plants of *C. kousa* or *C. nuttallii* but the peduncle length is clearly longer than that of the one known $F_1$ interspecific hybrid of *C. kousa*×*C. nuttallii* in commerce as 'KN4-43' (U.S. Plant patent application Ser. No. 10/741, 618) having an average length of 1.67 mm.

FLORAL BRACTS

Number: Typically 4 (in two opposing pairs; infrequently 5).
Size of floral bracts:

| | | Length of upper bracts (cm) | Width of upper bracts (cm) | Involucral spread (cm) | |
|---|---|---|---|---|---|
| Year | n | average | average | n | average |
| 1993 | 50 | 6.89 | 5.26 | 25 | 14.28 |
| 1997 | 20 | 8.06 | 6.32 | 10 | 16.52 |
| 1999 | 94 | 7.49 | 5.31 | 47 | 15.41 |
| 2002 | 40 | 7.20 | 6.10 | 20 | 14.68 |
| 2003 | 70 | 8.90 | 6.74 | 35 | 18.18 |

| | | Length of lower bracts (cm) | Width of lower bracts (cm) | Involucral spread (cm) | |
|---|---|---|---|---|---|
| Year | n | average | Average | n | Average |
| 1993 | 50 | 6.86 | 5.61 | 25 | 14.22 |
| 1997 | 20 | 8.01 | 6.43 | 10 | 16.41 |
| 1999 | 94 | 7.27 | 5.76 | 47 | 15.00 |
| 2002 | 40 | 7.20 | 6.57 | 20 | 14.71 |
| 2003 | 70 | 8.72 | 6.72 | 35 | 17.83 |

The size of the floral bracts on plants of 'KN30-8' varies from year to year due to the many environmental factors influencing the annual growth of trees. However, the floral bracts of our new hybrid are larger than those of any cultivar of *C. kousa* known to us and are larger than those of the six patented $F_1$ interspecific hybrids of *C. kousa*×*C. florida* ('Aurora'® U.S. Plant Pat. No. 7,205, 'Celestial'® U.S. Plant Pat. No. 7,204, 'Constellation'® U.S. Plant Pat. No. 7,210, 'Stardast'® U.S. Plant Pat. No. 7,206, 'Stellar Pink'® U.S. Plant Pat. No. 7,207 and 'Ruth Ellen'® U.S. Plant Pat. No. 7,732) in the trade today as well as the one and only $F_1$ interspecific hybrid of *C. kousa*×*C. nuttallii* ('KN4-43', plant patent applied for) and the $F_1$ interspecific hybrid 'Eddie's White Wonder' (*C. florida*×*C. nuttallii*) U.S. Plant Pat. No. 2,413. The floral bracts of 'KN30-8' are comparable in size to those of typical plants of *C. nuttallii* (bracts about 6 to 7.5 cm).

Color:
*Adaxial surface.*—Closest to 155A White Group.
*Abaxial surface.*—Closest to 155D White Group.
Shape: Globose.
Apex: Broadly apiculate.
Base: Attenuate.
Bract stalk length: 5 to 8 mm.
Bract stalk width: 5 to 6 mm.
Flower description: Very floriferous. Single flowers arranged in compact, dense heads subtended by the large floral bracts. No observed fragrance. Flowers not persistent. Floral display of the involucral bracts lasts about two to three weeks, depending on weather conditions.
Flowering habit: Anthesis of the tiny, relatively inconspicuous true flowers generally begins a few days following the onset of the ornamental display of the large floral bracts which generally occurs in central New Jersey about the last week of May and continues for 14 to 21 days depending on the prevailing weather conditions. Floral development is asynchronous within the inflorescence.
Number of true flowers per flower head:

| | | n |
|---|---|---|
| 1995 | 73.1 | 25 |
| 1996 | 69.7 | 10 |
| 1997 | 64.9 | 58 |
| 1998 | 67.3 | 14 |
| 1999 | 74.1 | 47 |
| 2001 | 72.0 | 25 |
| 2002 | 63.7 | 41 |
| 2003 | 69.4 | 35 |

The number of true flowers per flower head of our advanced generation interspecific hybrid is intermediate to that of the parent plants as the pistillate parent had about 70–80 flowers per flower head and the staminate parent (*C. kousa*) about 45–55 flowers per flower head.

REPRODUCTIVE ORGANS

Stamens:
*Number per flower.*—4.
*Color.*—Somewhat greenish white.
*Filament size.*—Approximately 2.5 mm long and 0.5 mm wide.
*Anther size.*—Approximately 1.1 mm long and 0.25 mm wide. Pollon is sparse in amount, and is somewhat brownish yellow.
Pistil:
*Number.*—1.
*Diameter.*—Approximately 0.75 mm.
*Color.*—Somewhat brownish yellow.
*Style plus stigma.*—About 2.25 mm long.

FRUIT

Flower head with fruit: Fruits are 2-celled, typically 1 seeded, fleshy, drupes that form a mounded raspberry-like syncarp approximately 2.5 cm in height and 2.5 cm in width with a flattened base. The many inferior ovaries are enclosed in a fleshy mass similar to the fruit of *C. kousa*. The exterior surface is quite smooth except for the dried floral parts at the tip of each individual inferior ovary; i.e., the sepals and the style and stigma which collectively appear as a minute brownish blotch (177A Greyed-Orange Group) in the mature fruit.
Seed:
*Color.*—165C Greyed-Orange Group.
*Size.*—6.5 mm long and 4.0 mm wide at center. Is basically rounded but narrows to an obtuse end at the base.

What is claimed is:

1. A new and distinct cultvar of dogwood tree, substantially as herein shown and described, comprising an advanced generation interspecific hybrid of *Cornus kousa*× *C. nuttallii* with *C. kousa*.

* * * * *